United States Patent
Kluger et al.

(10) Patent No.: US 9,308,103 B1
(45) Date of Patent: Apr. 12, 2016

(54) OSSEOINTEGRATED MOUNT FOR PROSTHETIC LIMB AND PERIPHERAL NERVE INTERFACE

(71) Applicants: David T. Kluger, Salt Lake City, UT (US); David J. Warren, Salt Lake City, UT (US); Gregory A. Clark, Salt Lake City, UT (US); Kent N. Bachus, Salt Lake City, UT (US)

(72) Inventors: David T. Kluger, Salt Lake City, UT (US); David J. Warren, Salt Lake City, UT (US); Gregory A. Clark, Salt Lake City, UT (US); Kent N. Bachus, Salt Lake City, UT (US)

( * ) Notice: Subject to any disclaimer, the term of this patent is extended or adjusted under 35 U.S.C. 154(b) by 120 days.

(21) Appl. No.: 14/464,069

(22) Filed: Aug. 20, 2014

Related U.S. Application Data (60) Provisional application No. 61/959,301, filed on Aug. 20, 2013.

(51) Int. Cl.
*A61F 2/78* (2006.01)
*A61F 2/80* (2006.01)
*A61F 2/60* (2006.01)
*A61F 2/54* (2006.01)

(52) U.S. Cl.
CPC ... *A61F 2/80* (2013.01); *A61F 2/54* (2013.01); *A61F 2/60* (2013.01)

(58) Field of Classification Search
CPC .. A61F 2/2814; A61F 2/78; A61F 2002/7887
See application file for complete search history.

(56) References Cited

U.S. PATENT DOCUMENTS

| | | | |
|---|---|---|---|
| 4,158,895 | A | 6/1979 | Reswick et al. |
| 4,938,769 | A | 7/1990 | Shaw |
| 5,906,644 | A | 5/1999 | Powell |
| 6,485,522 | B1 | 11/2002 | Grundei |
| 8,512,416 | B2 | 8/2013 | Porter et al. |
| 2002/0038148 | A1 | 3/2002 | Fernandez et al. |
| 2004/0068324 | A1 | 4/2004 | Grundei |
| 2005/0021471 | A1 | 1/2005 | Zlotnick |

(Continued)

FOREIGN PATENT DOCUMENTS

| | | |
|---|---|---|
| DE | 202004014043 U1 | 12/2004 |
| EP | 1529501 B1 | 7/2006 |

(Continued)

OTHER PUBLICATIONS

Acta Orthop Scand. 1981;52(2):155-70. Abstract—Osseointegrated titanium implants. Requirements for ensuring a long-lasting, direct bone-to-implant anchorage in man. Albrektsson, T., et al.
Titanium Alloys in Medical Applications, pp. 1-3, retrieved on Dec. 2, 2013 from URL:http://www.azom.com/article.aspx?ArticleID=1794, The Titanium Information Group, UK.

*Primary Examiner* — Bruce E Snow
(74) *Attorney, Agent, or Firm* — Barnes & Thornburg LLP (57) ABSTRACT

The invention includes an osseointegrated mount and electrical connector, suitable for providing neural control and sensory feedback for an advanced prosthetic limb. The device provides a channel in which a lead wire from the peripheral nerve interface can travel from the electrical connector down the side of the device or within the device to limit potential sites of infection to a single transcutaneous breach. The channel allows for a silicone barrier to be installed between the internal and external components.

10 Claims, 8 Drawing Sheets

(56) References Cited

U.S. PATENT DOCUMENTS

| | | |
|---|---|---|
| 2005/0102038 A1 | 5/2005 | Grundei |
| 2009/0005820 A1 | 1/2009 | Bloebaum et al. |
| 2009/0036908 A1 | 2/2009 | Zokol et al. |
| 2009/0187256 A1 | 7/2009 | Rauguth et al. |
| 2010/0016992 A1* | 1/2010 | Malawer ............... A61F 2/2814 623/33 |
| 2010/0222893 A1 | 9/2010 | Dorr et al. |
| 2011/0257758 A1 | 10/2011 | Smith et al. |
| 2013/0166009 A1 | 6/2013 | Branemark et al. |
| 2014/0156022 A1 | 6/2014 | Holt et al. |
| 2014/0195002 A1 | 7/2014 | Bachus et al. |
| 2015/0305897 A1* | 10/2015 | Hershberger ............ A61F 2/78 623/32 |

FOREIGN PATENT DOCUMENTS

| | | |
|---|---|---|
| WO | 03084429 A3 | 12/2003 |
| WO | 2009105535 A1 | 8/2009 |
| WO | 2012026870 A1 | 3/2012 |
| WO | 2013048589 A1 | 4/2013 |

* cited by examiner

OSSEOINTEGRATED MOUNT FOR PROSTHETIC LIMB AND PERIPHERAL NERVE INTERFACE

This application claims priority to U.S. Provisional Application No. 61/959,301, filed Aug. 20, 2013.

BACKGROUND OF THE INVENTION

Advanced prosthetic arms have been developed that communicate with a high-channel count neural interface implanted in residual peripheral nerves capable of reading multiple, independent motor signals (via recording), and providing sensory cutaneous and proprioceptive information (via stimulation), to give amputees unprecedented control over their motorized exoprostheses, particularly prostheses with high degrees of freedom.

The key technical limitation is not the development of an advanced arm itself, which largely has been accomplished, but instead includes 1) a method of attaching the arm reliably to the body; and 2) a means of communicating bidirectionally with the arm, to provide control signals and to obtain sensory information.

Socket-type attachment of an artificial limb (exoprosthesis) to the residual limb is the current standard of care, but is often inadequate. The technology often fails when applied to short residual limbs and can cause discomfort, pain, and severe soft-tissue necrosis. Consequently, alternative docking systems, Percutaneous Osseointegrated Prostheses (POPs), are being developed that typically have three basic components: (1) an endoprosthesis that attaches to and integrates with bone, (2) a subdermal barrier to infection, and (3) a load-bearing percutaneous post. Despite some successes, infection remains a serious problem, and comparable clinical devices for people with upper-limb loss have not been perfected.

Progress has been made in the development of long-term POPs that provide direct attachment to the user's skeleton and direct communication with the user's motor and sensory neurons within nerves, via a peripheral nerve interface such as the Utah Slanted Electrode Array (USEA) or other high-channel count neural interface communicating with peripheral nerves, yet further design is warranted. Advances in structural integrity, protection of the fragile wiring of peripheral nerve interfaces, resistance against infections introduced by transcutaneous breaches, and ease of assembly and implantation could be beneficial for providing amputees with desired comfort and control of motorized artificial arm.

SUMMARY OF THE INVENTION

The invention includes an osseointegrated mount and electrical connector, suitable for providing neural control and sensory feedback for an advanced prosthetic limb. The device includes an implantable endoprosthesis component configured to be osseointegratable. A connector mount aligns with the endoprosthesis component. Both components include a channel in which one or more wires can be disposed for connection to a high-channel count neural interface. A barrier is disposed in the channel in the surface of the connector mount. A cover component, complimentary in shape to a portion of the connector mount and connectable thereto, protects wire(s) within the channel. The endoprosthesis component and connector mount have boreholes extending through them to accommodate a pylon. A bolt is positioned in a borehole in the pylon and extends into the endoprosthesis component to which it is threadedly secured.

The invention further includes a method of attaching a prosthetic device to a residual limb. The method comprises providing a mount for a prosthetic device according to the embodiments provided herein. The endoprosthesis component is implanted and a cavity cover is attached. The skin and soft tissue are sutured closed. After a period during which the device osseointegrates, the skin around the endoprosthesis component is reopened and the cavity cover is removed. A peripheral nerve interface assembly and the pylon are then mounted to the endoprosthesis component. The bolt is disposed within the pylon and threadedly engaged with the endoprosthesis component so secure the connector mount and pylon to the endoprosthesis component, thereby creating a mechanically coupled peripheral nerve interface and percutaneous osseointegrated prosthetic device.

BRIEF DESCRIPTION OF THE DRAWINGS

The invention is best understood from the following detailed description when read in conjunction with the accompanying drawings. All drawings are of illustrative embodiments of the invention.

DETAILED DESCRIPTION OF THE INVENTION

The invention includes an osseointegrated mount and electrical connector, suitable for providing neural control and sensory feedback for an advanced prosthetic limb. The disclosed invention has applications to lower and upper limbs but is particularly suitable for upper limb use. Bidirectional neural communication is typically more desired in upper limb prostheses because dexterous hand movements and object manipulation are upper limb tasks. However, socket problems are more prevalent in lower limb prostheses, which the osseointegration features reduce or eliminate.

The disclosed device integrates the osseointegrated mount for a prosthetic limb with the electrical connector that functionally connects a peripheral nerve interface, for example a Utah Slanted Electrode Array (USEA), which is a high-channel count neural interface implanted in residual peripheral nerves, to the prosthetic limb. The disclosed device allows a lead wire from the peripheral nerve interface to travel from the electrical connector down the side of the device, or within the device, thereby limiting potential sites of infection to a single transcutaneous breach. A channel in which the lead wire sits allows for a silicone barrier to be installed between the internal and external components. Other barrier materials or mechanisms may be used, provided they inhibit or prevent foreign material from entering into the body and, conversely, body fluids from coming in contact with the connector. The device components should be biocompatible as necessary and maintain electrical continuity where applicable.

FIGS. 1A-H depict a mount apparatus for a prosthetic device in various stages of assembly, according to an illustrative embodiment of the invention. As can be seen in FIGS.

Figure 1A:
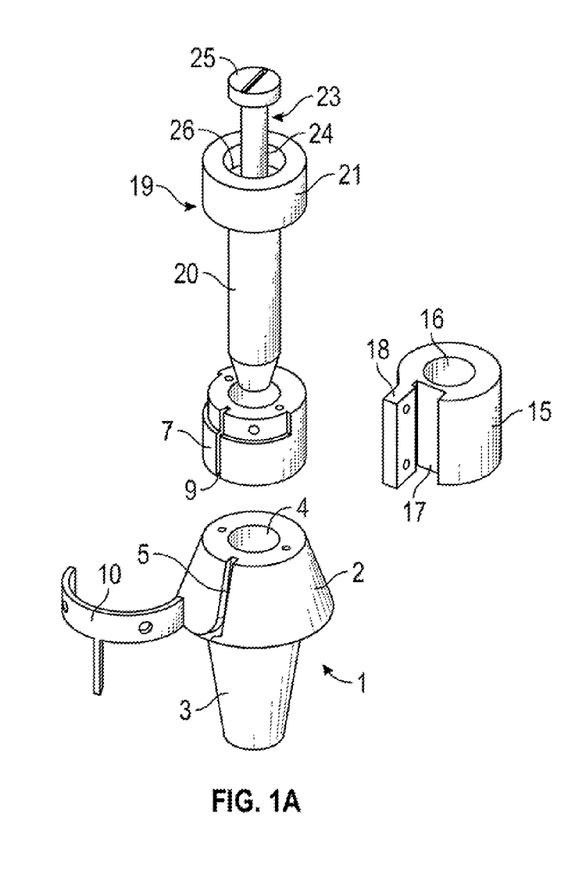
FIGS. 1A-H depict a mount apparatus for a prosthetic device in various stages of assembly.
Figure 1B:
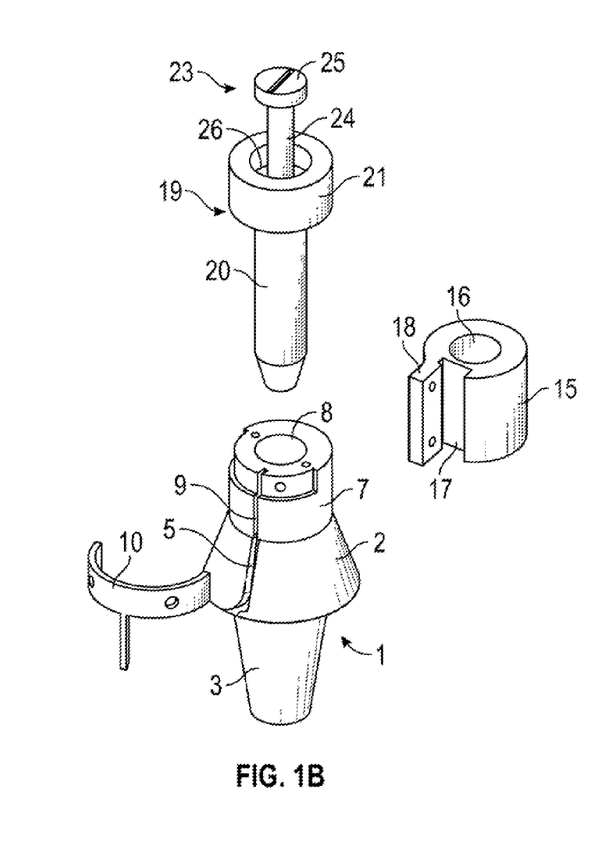
Figure 1C:
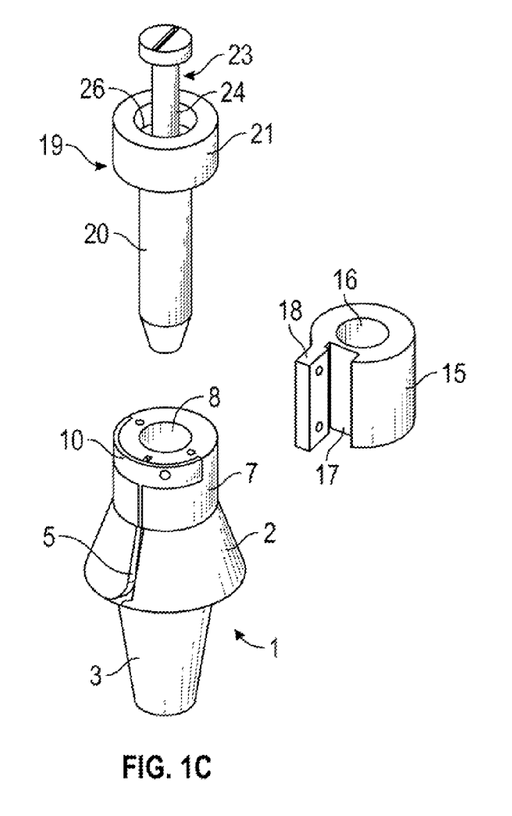
Figure 1D:
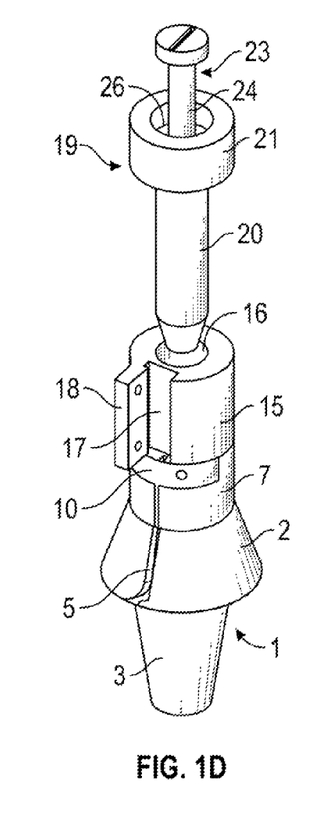
Figure 1E:
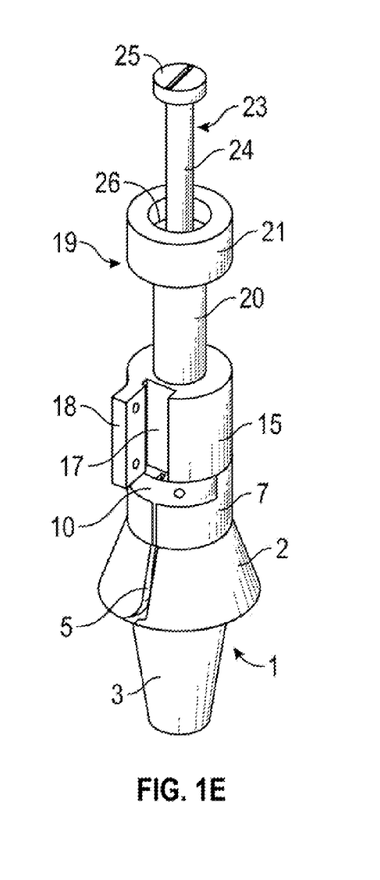
Figure 1F:
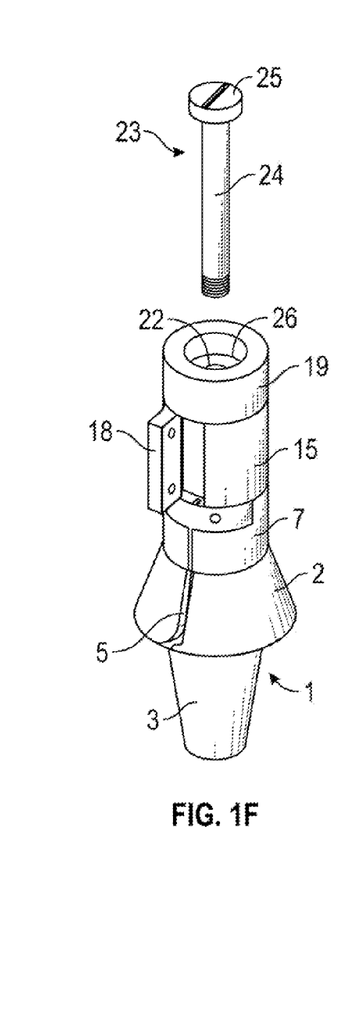
Figure 1G:
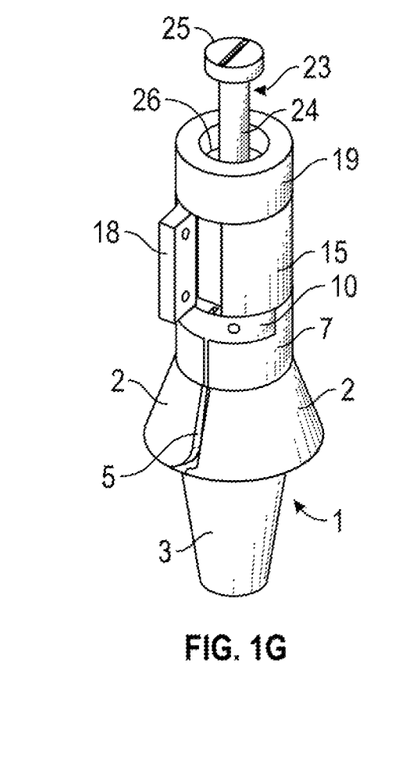
Figure 1H:
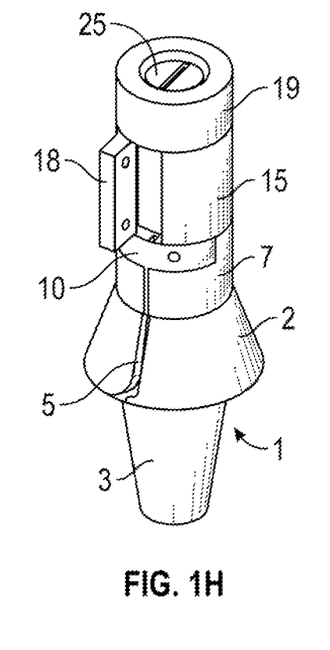
Figure 2:
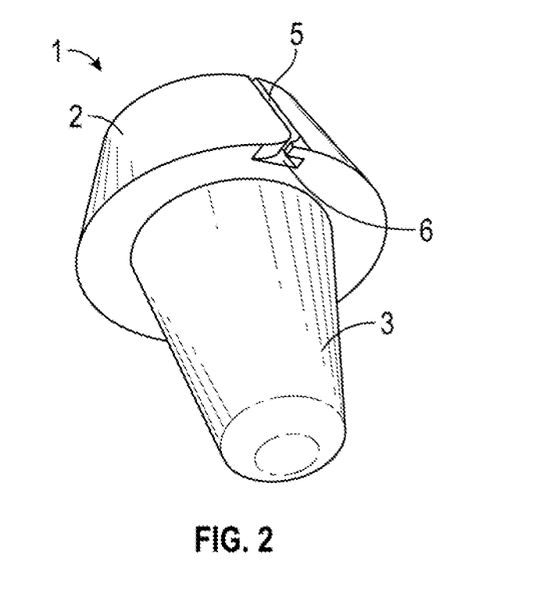
FIG. 2 depicts an endoprosthesis component.

1A-H, and more particularly in FIG. 2, an endoprosthesis component 1 is provided for internal placement in an individual. Endoprosthesis component 1 has a first conical section or subcutaneous collar 2 and a second conical section 3. As shown in FIG. 2, "conical" is intended to mean in this instance, a conical-like shape having a cropped apex end. Second conical section 3 extends into the bone to anchor the endoprosthesis component 1 into the distal end of residual bone, via osseointegration. First conical section 2 lies beneath the residual limb's skin. Skin ingrowth allows for a natural skin barrier to form over it. Where osseointegration is desired, a porous titanium surface may be used. Other surfaces or materials can be used provided they facilitate bone growth around first conical section 2, and preferably with little or no fibrous tissue formation at the interface. PEEK as well as silicon nitride can be made into porous coatings that allow for similar ingrowth. Titanium need not be pure. An alloy, such as Ti-6Al-4V (titanium with 6% aluminum and 4% vanadium impurities) can be used.

In the illustrative embodiment shown in FIG. 2, each conical section 2, 3 has a base, which is the larger diameter end of the conical section, and an apex, which is the smaller diameter end of the conical section. The bases of the first and second conical sections 2, 3 abut one another with their longitudinal center lines in line with one another. Endoprosthesis component 1 has a borehole 4 extending at least partially longitudinally through it from the first conical section apex end. The borehole must extend sufficiently into endoprosthesis component 1 so that it will have the structural integrity necessary to accommodate bolt 23, which will be described further below. Variations in the specific geometry of endoprosthesis component 1 can be used provided they can be appropriately and securely anchored in the bone.

As shown in FIG. 2, a channel 5 extends into the surface of the first conical section 2 and runs from its base to its apex. Channel 5 has a hook-shaped cross-sectional profile 6 to accommodate a wire in the hook portion. The hook-shaped portion 6 may be for example, J-shaped, L-shaped or another profile that helps to retain the wire in the channel. The "hook shape" allows the wire to be readily inserted into channel 5 but serves to hold it in channel 5, and possibly protect it, by surrounding it to a greater extent than if it were in a channel with a rectangular profile for example. Multiple channels may be provided for use with multiple peripheral nerve interfaces or multiple wires from a single interface. Wires may be for example, on the order of about 0.1 mm to about 2 mm in diameter and comprise platinum or other suitable material. The specific wires housed in channel 5 will depend on the application. Edges over which wires may extend or come in contact with are preferable rounded, for example those shown at the base end of channel 5 in FIG. 2.

Figure 3:
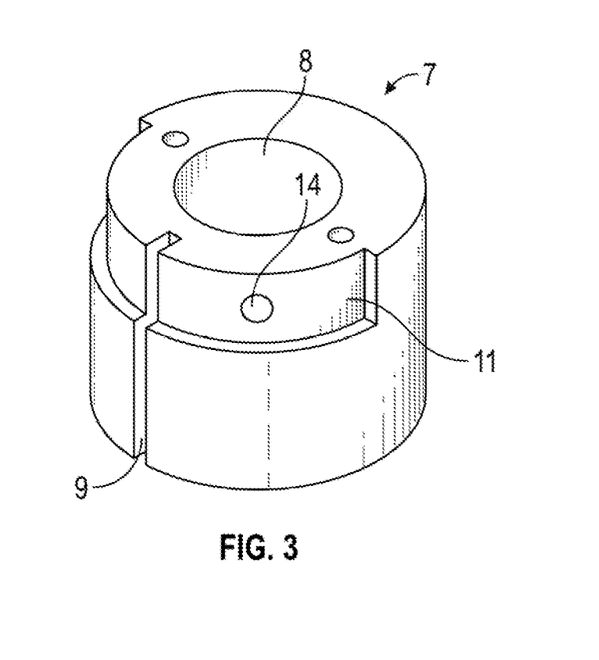
FIG. 3 shows a first connector mount section.

The prosthetic device mount includes a first connector mount section 7, as shown in FIG. 3, having an outer diameter substantially the same as the outer apex diameter of the first conical section 2. The cylindrical shapes depicted in the figures are suitable or preferred for most applications, however, variations in cross-sectional shapes can be used when appropriate. The connector mount, in this embodiment comprising a first and second section, is provided to attach or secure an electrical connector of selected channel number, to functionally connect one or more wires from a peripheral nerve interface to a prosthetic device. First connector mount section 7 has a longitudinal borehole 8 extending though its length. First connector mount section 7 has a channel 9 extending into its surface and running longitudinally from top to bottom. As shown in FIG. 1B, first connector mount section 7 fits on top of endoprosthesis component 1 so that borehole 4 and borehole 8 are aligned, and channel 5 and channel 9 are aligned. First connector mount section 7 is positioned partially beneath the skin. It can be coated with a porous titanium material, or other coating that promotes skin ingrowth. Although shown as cylindrical here, first connector mount section 7 can have other shapes, but must be structurally compatible with endoprosthesis component 1, and must accommodate, house, or align a wire that will also extend into channel 5 in endoprosthesis component 1.

Figure 4:
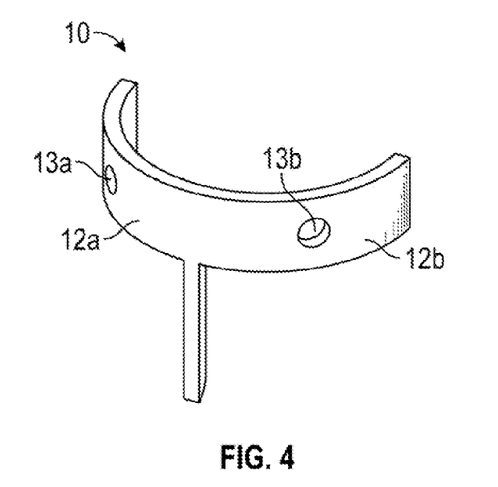
FIG. 4 shows a protective wire cover.

A cover 10, shown in FIG. 4, is complimentary in shape to a portion 11 of the surface of first connection mount section 7 and configured to cover channel 9, as can be seen in FIG. 1C. A barrier, for example comprising silicone, is disposed between cover 10 and first connector mount section 7 in channel 9. Cover 10, when positioned on first connector mount section 7, leaves space for one or more wires to reside within channel 9. Cover 10 has at least one flange, shown in FIG. 4 as two flanges 12a, 12b, complimentary in shape to an indentation in first connector mount section 7. Flanges 12a, 12b provide structure to secure cover 10 to first connector mount section 7. Holes 13a, 13b in flanges 12a, 12b are provided through which fasteners such as threaded bolts can be disposed to engage first connector mount section 7. First connector mount section 7 has holes 14 (one of which is shown) that can be threaded to receive and engage the fasteners. Cover 10 can overlap various portions of first connector mount section 7. It can fully surround first connector mount section 7, or partially surround it as in FIG. 4. Cover 10 at a minimum protects a wire in channel 9 and provides a means for attachment to first connector mount section 7.

Figure 5:
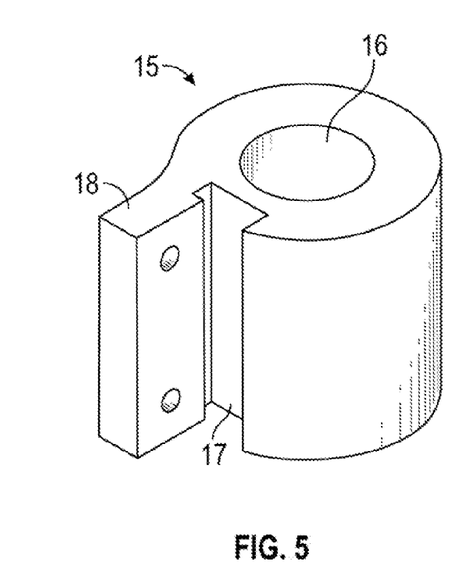
FIG. 5 shows a second connector mount section.

A second connector mount section 15, as shown in FIG. 5, is provided to house and support one or more electrical connectors. Second connector mount section 15 has an outer diameter substantially the same as the outer diameter of first connector mount section 7. Second connector mount section 15 has a borehole 16 extending longitudinally through it. A channel 17 in the surface of second connector mount section 7 runs longitudinally from the top to the bottom. A flange 18 extends longitudinally along an edge of channel 17. Flange 18 provides a surface to which a connector cover can be attached. As depicted in FIG. 1D, second connector section 15 fits on top of first connector section 7 so that channels 9 and 17 and boreholes 8 and 16 are aligned. A connector cover that protects channel 17 can also extend to protect channel 9 so that cover 10 may either be eliminated or modified accordingly.

Figure 6:
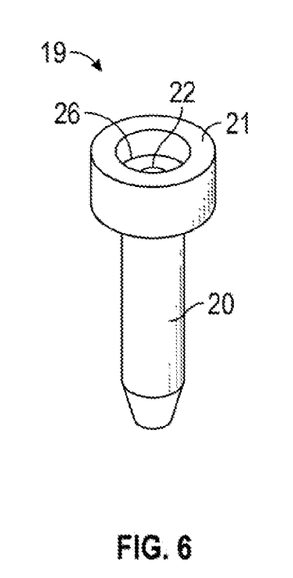
FIG. 6 depicts a pylon.

FIG. 6 depicts a pylon 19 having a shaft 20 and a head 21. Pylon 19 provides a prosthetic limb attachment site. A borehole 22 extends longitudinally through pylon 19. Shaft 20 has an outer diameter smaller than boreholes 4, 8, 16 in first connector mount section 7, second connector mount section 15, and endoprosthesis component 1, respectively. The difference in the outer diameter of shaft 20 and inner diameters of boreholes 4, 8, 16 is preferably small enough to provide a close fit and minimize relative lateral movement between the parts. The cross-sectional area of head 21 is shown as cylindrical, but may be pyramid-shaped, depending on the prosthesis with which it is used. As shown in FIGS. 1E, 1F, pylon 19 is inserted into second connector mount section 15, further through first connector mount section 7, and still further into endoprosthesis component 1.

Figure 7:
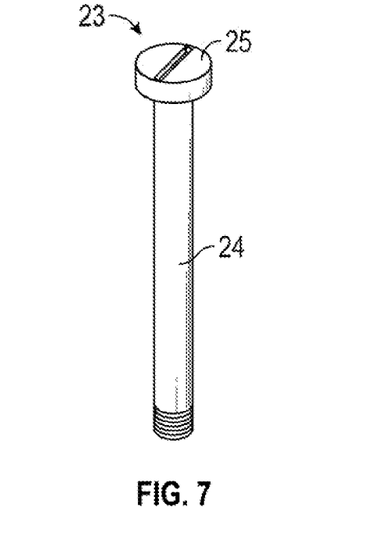
FIG. 7 shows a bolt.

FIG. 7 depicts a bolt 23 having a shaft 24 and a head 25. FIGS. 1F-H show bolt 23 being inserted into boreholes 8, 16, 4, in that order to secure the components to bone-anchored endoprosthesis component 1. At least a portion of bolt shaft 24 is threaded to engage complimentary threads in borehole 4. When bolt 23 engages endoprosthesis component 1, it holds together endoprosthesis component 1, first connector mount section 7, second connector mount section 15 and pylon 19. When bolt 23 is fully inserted, the aforementioned four components will preferably not move longitudinally with respect to one another. Bolt head 25 may be flush with a top surface of pylon head 21 or sit within a well 26 of larger diameter than borehole 22 so as to countersink bolt 23 in pylon 19.

Figure 8:
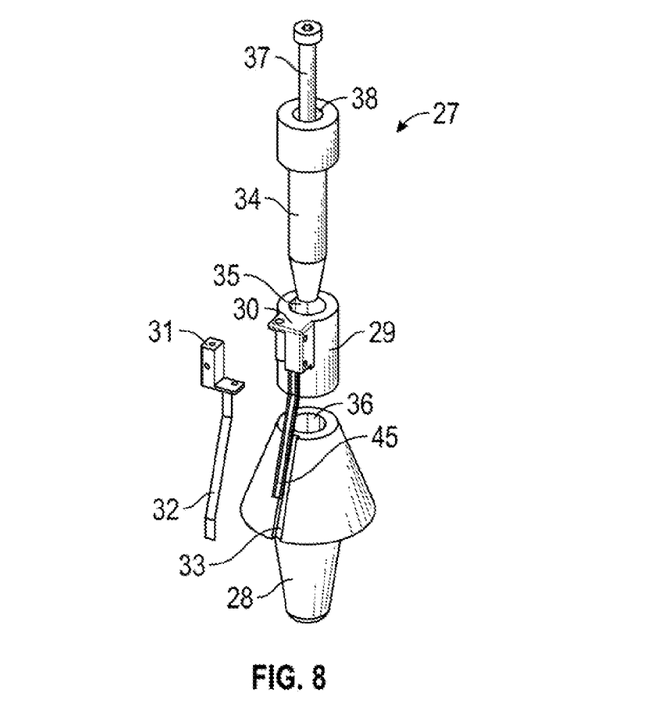
FIG. 8 depicts an osseointegrated mount assembly.

FIG. 8 depicts an osseointegrated mount assembly 27 according to another illustrative embodiment of the invention, in which the connector is a single component, in this case which is shown as cylindrical. Endoprosthesis component 28 abuts cylindrical connector mount 29. Cylindrical connector mount 29 has a housing portion 30 on its exterior surface to which a peripheral nerve interface connector can be mounted. A housing wire channel 45 extends from housing portion 30 and fits in a channel 33 of endoprosthesis component 28. Wire cover 31 completes the connector housing. A cover extension 32 extends to cover housing wire channel 45 and channel 33 in endoprosthesis component 28. As in the previous embodiments described, channel 33 can house one or more lead wires to the peripheral nerve interface. A pylon 34 extends into a borehole 35 in cylindrical connector mount 29 and borehole 36 in endoprosthesis component 28. A bolt 37 extends through borehole 38 in pylon 34.

Figure 9:
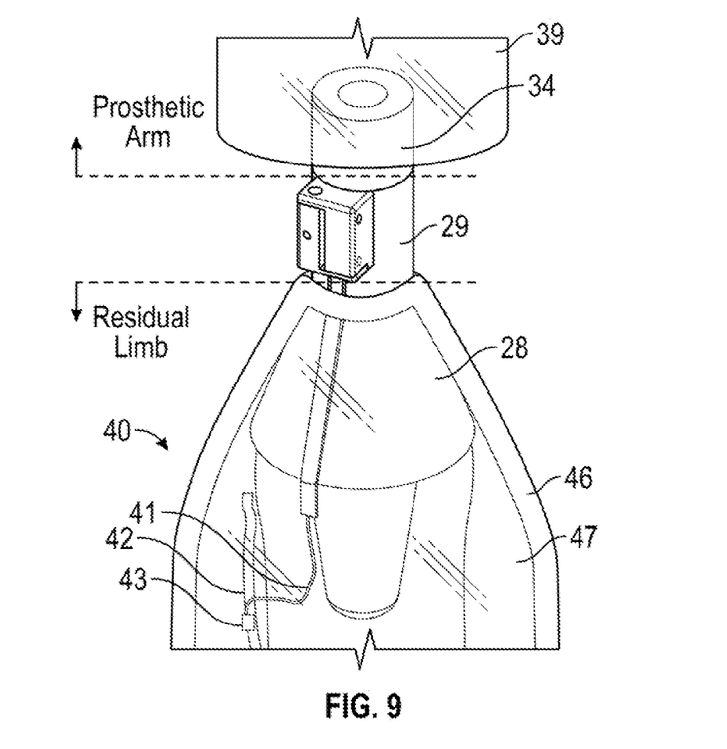
FIG. 9 depicts an implanted osseointegrated mount assembly.

FIG. 9 depicts an implanted osseointegrated mount assembly 27 according to an illustrative embodiment of the invention. Pylon 34 is disposed at least partially within prosthetic limb 39. Cylindrical connector mount 29 is external to prosthetic limb 39 and also to a residual limb 40. Endoprosthesis component 28 is implanted into residual limb 40, beneath skin 46 and partially within bone 47. Lead wire 41 extends in channel 33 from a connector secured in cylindrical connector mount 29 to a nerve 42 in residual limb 40. Lead wire 41 is electrically connected to a peripheral nerve interface 43.

Wiring has been described as extending through one or more channels, for example as in connector mount sections 7, 15, and a portion of endoprosthesis component 1 or endoprosthesis component 28. These channels are depicted as having separate covering components. The channels though may be either entirely or partially within the device components, thereby eliminating the cover components or allowing for variations in the cover component features.

Break-away internal connections can be provided, which would allow either the peripheral nerve interface or the endoprosthesis to be explanted if necessary without compromising the function of the other. More than one type of these subcutaneous connectors may be needed to allow a break in connection near the peripheral nerve interface or near the cutaneous breach around the peripheral nerve interface connector mount.

Components of the ossiointegrated mount may be constructed, for example, of titanium or other medical-grade materials. Various surface-treatments of subcutaneous parts may be used to promote osseointegration.

Specific dimensions of components and relative dimensions of components will vary depending on the application of the device. Illustrative quantities include:
  endoprosthesis component 1—total length 45 mm
    first conical section 2 or subcutaneous collar
      length 15 mm
      apex diameter 20 mm
      base diameter 30.92 mm
    second conical section 3
      length 30 mm
      apex diameter 6.35 mm
      base diameter 20 mm
    relative lengths of sections 2 and 3—3:4
    borehole 4—diameter 10 mm
    channel 5—depth 2.37
      hook-shaped cross-sectional profile 6—curvature diameter) 4 mm
  pylon 19
    outer diameter close fit to 20 mm diameter borehole 4
    borehole diameter 5 mm Dimensions can be scaled or modified for different device types, sizes and uses. Illustrative dimension ranges that comprise dimensions for both upper and lower limb use are:
  Full length: 75 mm to 450 mm
  Intramedullary length: 45 mm—420 mm
  Largest diameter: 10 mm to 200 mm
  Intramedullary diameter: 10 mm—40 mm.

Illustrative dimensions of devices used for animal studies are:
  Full length: 25 mm
  Intramedullary length: 10 mm
  Largest diameter: 3 mm
  Intramedullary diameter: 3 mm.

The various ratios of the dimensions are also a part of illustrative embodiments of the invention.

Implantation of the osseointegrated mount utilizes a two-stage surgical procedure. In stage one, the internal components of the device are implanted, and the skin and soft tissues are sutured closed. The internal components include endoprosthesis component 1 having first conical section (subcutaneous collar) 2 and second conical section 3. Cavity cover 44 (described below) is also implanted to prevent tissue growth into cavity 4 during osseointegration period. A postoperative period (e.g., about six months) allows the device to osseointegrate substantially before it bears loads from a prosthetic limb. In stage two, the skin around the first conical section 2 is reopened so the peripheral nerve interface assembly and pylon 19 can be mounted to the stage one components. Bolt 23, running through the entire device, is screwed into endoprosthesis component 1. The bolt secures components 7, 15, and 19 to the internal osseointegrated components, creating a mechanically coupled peripheral nerve interface and percutaneous osseointegrated prosthetic device.

Figure 10:
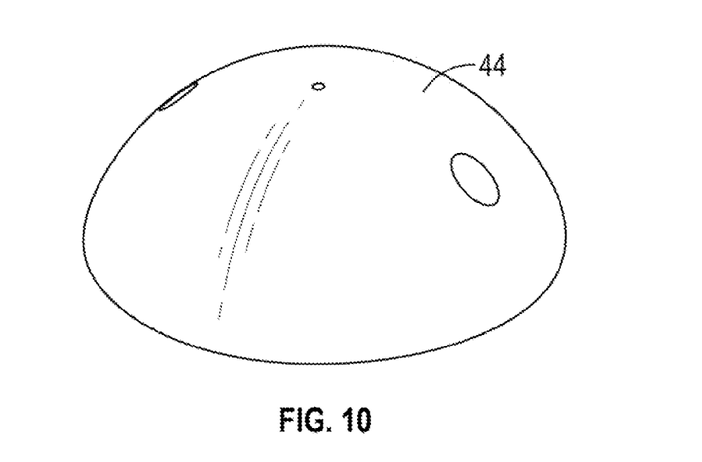
FIG. 10 depicts a temporary cavity cover.

FIG. 10 depicts a temporary cavity cover 44 that is implanted during stage one surgery. It is beneficial to cover up unsealed cavities beneath the skin during an osseointegration period for two reasons: 1) prevents unwanted growth of soft tissues into the cavities where stage two elements will need to be, and 2) allows for proper soft tissue growth around the implant during this period. The cavity cover does not directly touch connector mount section 7. Instead it attaches to the endoprosthesis component.

In addition to threaded bolt 23 that mates with threads in borehole 4 in endoprosthesis component 1, there are also smaller screws to attach components together and associated threaded holes. Small bolts are needed in the stage one and two procedures. In stage one, cavity cover 44 is connected to endoprosthesis component 1. In stage two, the aforementioned small bolts are removed and two longer ones connect connector mount section 7 to endoprosthesis component 1. See for example FIG. 7 showing boreholes on the top surface of first connector mount section 7. Two small bolts are also used to connect wire cover 10 to connector mount section 7, which have threading in holes that face radially outwards from the curved surface, but not in holes that face axially out of the flat areas. Connector mount section 15 does not require bolts in the design presented above, but could utilize to connect with connector mount section 7.

Various embodiments of the invention have been described, each, which may have a different combination of elements. The invention is not limited to the specific embodiments disclosed, and may include different combinations of the elements disclosed or omission of some elements and the equivalents of such structures.

The invention claimed is:
1. A mount for a prosthetic device comprising:
an endoprosthesis component;
the endoprosthesis component configured to be osseointegratable;
the endoprosthesis component having a borehole therethrough;
a channel in the endoprosthesis component extending at least along a portion of the length of the endoprosthesis component;
a connector mount having a longitudinal borehole therethrough;
the connector mount having a surface and a channel extending longitudinally along the surface of the connector mount alignable with the endoprosthesis component channel;
a cover component complimentary in shape to a portion of the connector mount and connectable thereto, wherein when connected to the connector mount a space between the cover component and the connector mount exists to accommodate one or more wires;
the channel in the surface of the connector mount configured to accommodate a barrier;
a pylon having a longitudinal borehole therethrough;
the pylon having an outer diameter smaller than the boreholes in the connector mount and the endoprosthesis component;
a bolt having threads on at least a portion;
the bolt sized to fit through the boreholes in the pylon and connector mount;
wherein the bolt is threadedly engageable in the borehole of the endoprosthesis component.

2. The mount for a prosthetic device of claim 1 wherein the endoprosthesis component comprises:
a first conical collar section having a base and a second conical section having a base, the bases of which abut one another, and the longitudinal center lines of the first and second conical sections in line with one another.

3. The mount for a prosthetic device of claim 1 wherein the channel has a hook-shaped cross-sectional profile.

4. The mount for a prosthetic device of claim 1 wherein the connector mount comprises:
a first connector mount section;
a second connector mount section having an outer diameter substantially the same as the outer diameter of the of the first connector mount section; and
wherein the channel extends longitudinally along the surface of the fist and second connector mount sections.

5. The mount for a prosthetic device of claim 4 wherein the cover component is configured to cover the channel in the first connector mount section.

6. The mount for a prosthetic device of claim 4 comprising:
a flange extending longitudinally along a channel edge of the second connector mount section.

7. The mount for a prosthetic device of claim 4 wherein the first connector mount section and the second connector mount section are cylindrical and the first and second connector mounts have diameters that are substantially the same and the diameter of the first connector mount section is substantially the same as the diameter of an end surface of the endoprosthesis component.

8. The mount for a prosthetic device of claim 1 wherein the connector mount has a flange extending longitudinally along at least a portion of the channel edge.

9. A method of attaching a prosthetic device to a residual limb comprising:
providing a mount for a prosthetic device according to claim 1;
implanting the endoprosthesis component and cover;
suturing the skin and soft tissues closed;
allowing a post operative period during which the device osseointegrates;
reopening the skin around the endoprosthesis component;
removing the cavity cover;
mounting a peripheral nerve interface assembly and the pylon to the endoprosthesis component; and
screwing the bolt into the endoprosthesis component to secure the connector mount and pylon to the endoprosthesis component thereby creating a mechanically coupled peripheral nerve interface and percutaneous osseointegrated prosthetic device.

10. A mount for a prosthetic device comprising:
an endoprosthesis component having a first conical collar section having a base and a second conical section having a base, the bases of which abut one another, and the longitudinal center lines of the first and second conical sections in line with one another;
the endoprosthesis component configured to be osseointegratable;
the endoprosthesis component having a borehole therethrough;
the first conical section having a surface;
a channel in the first conical section surface extending from the base to an apex, the channel having a hook-shaped cross-sectional profile;
a first cylindrical connector mount section having an outer diameter substantially the same as the first conical section apex outer diameter and having a longitudinal borehole there through;
a channel extending longitudinally along the surface of the first cylindrical connector mount section;
a cover component complimentary in shape to a portion of the first cylindrical connection mount section surface and configured to cover the first cylindrical connector mount section channel;
the cover having at least one flange complimentary in shape to an indentation in the first cylindrical connector mount section;
a second cylindrical connector mount section having an outer diameter substantially the same as the outer diameter of the of the first cylindrical connector mount section;
a channel extending longitudinally along the surface of the second cylindrical connector mount section;
a barrier disposed in the channel in the surfaces of the first and second connector mounts;
a flange extending longitudinally along a channel edge of the second cylindrical connector mount section;
a pylon having a shaft and a head and a longitudinal borehole therethrough;
the pylon having an outer diameter smaller than the boreholes in the first and second cylindrical connector mount sections and the endoprosthesis component;
a bolt having a shaft, the shaft having threads on at least a portion;
the bolt sized to fit through the boreholes in the pylon, and first and second cylindrical connector mount sections; and
the bolt threadedly engageable in the borehole of the endoprosthesis component.

* * * * *